United States Patent
Carmeliet

(10) Patent No.: US 6,930,089 B2
(45) Date of Patent: Aug. 16, 2005

(54) USE OF VASCULAR ENDOTHELIAL GROWTH FACTOR, PLACENTA GROWTH FACTOR OR BOTH FOR PREVENTING OR TREATING ISCHEMIC DISEASE OR STROKE

(75) Inventor: Peter Carmeliet, Oud-Heverlee (BE)

(73) Assignees: D. Collen Research Foundation vzw, Leuven (BE); Flanders Interuniversity Institute for Biotechnology, VIB, Zwijnaarde (BE)

(*) Notice: Subject to any disclaimer, the term of this patent is extended or adjusted under 35 U.S.C. 154(b) by 29 days.

(21) Appl. No.: 10/182,359
(22) PCT Filed: Feb. 5, 2001
(86) PCT No.: PCT/EP01/01208
§ 371 (c)(1), (2), (4) Date: Sep. 23, 2002
(87) PCT Pub. No.: WO01/56593
PCT Pub. Date: Aug. 9, 2001

(65) Prior Publication Data
US 2003/0054995 A1 Mar. 20, 2003

Related U.S. Application Data
(60) Provisional application No. 60/236,594, filed on Sep. 29, 2000.

(30) Foreign Application Priority Data
Feb. 4, 2000 (GB) .............................. 0002527

(51) Int. Cl.⁷ .................... A61K 38/00; C07K 14/00
(52) U.S. Cl. ................ 514/12; 514/2; 530/399; 530/350
(58) Field of Search .................. 514/12, 2; 530/399, 530/350

(56) References Cited

FOREIGN PATENT DOCUMENTS

| GB | 2 332 373 A | 6/1999 |
|---|---|---|
| WO | WO 97/14307 A1 | 4/1997 |
| WO | WO 98/07832 A1 | 2/1998 |
| WO | WO 98/493 A1 | 11/1998 |
| WO | WO 99/40197 A2 | 8/1999 |

OTHER PUBLICATIONS

Domenico Maglione, Valente Guerriero, Giuseppe Viglieto, Pasquale DLLI–BOVI and M. Graziella Persico, Isolation of a human placenta cDNA coding for a protein related to the vascular permeability factor, Proc. Natl. Acad. Sci. USA, vol. 88, pp. 9267–9271, Oct., 1991 Biochemistry.

Frelin, "VEGF: A mediation of hypoxic angiogenesis", Medicine Sciences, vol. 13, no. 6–7, 1997, pp 886–892.

*Primary Examiner*—Janet Andres
(74) *Attorney, Agent, or Firm*—Barnes & Thornburg

(57) ABSTRACT

Vascular endothelial growth factor, placenta growth factor or combinations of both including heteodimers are useful in the treatment or prevention of stroke or ischemic diseases in mammals.

13 Claims, No Drawings

USE OF VASCULAR ENDOTHELIAL GROWTH FACTOR, PLACENTA GROWTH FACTOR OR BOTH FOR PREVENTING OR TREATING ISCHEMIC DISEASE OR STROKE

This application claims the benefit of provisional application 60/236,594 filed on Sep. 29, 2000.

The present invention relates to the prevention and treatment of strokes and ischemic diseases, in particular ischemic cerebral infarction, acute myocardial infarction and chronic heart disease, by means of specific growth factors. More particularly, this invention deals with the use of vascular endothelial growth factor, placenta growth factor or both in pharmaceutical compositions and methods for such prevention or treatment.

BACKGROUND OF THE INVENTION

Stroke, defined as a sudden weakening or loss of consciousness, sensation and volontary motion caused by rupture or obstruction of an artery of the brain, is the third cause of death in the United States. Worldwide, stroke is the number one cause of death due to its particularly high incidence in Asia. Ischemic stroke is the most common form of stroke, being responsible for about 85% of all strokes, whereas hemorrhagic strokes (e.g. intraparenchymal or subarachnoid) account for the remaining 15%. Due to the increasing mean age of the population, the number of strokes is continuously increasing. Because the brain is highly vulnerable to even brief ischemia and recovers poorly, primary prevention in ischemic stroke prevention offers the greatest potential for reducing the incidence of this disease.

Focal ischemic cerebral infarction occurs when the arterial blood flow to a specific region of the brain is reduced below a critical level. Cerebral artery occlusion produces a central acute infarct and surrounding regions of incomplete ischemia (sometimes referred to as 'penumbra'), that are dysfunctional—yet potentially salvageable. Ischemia of the myocardium, as a result of reduced perfusion due to chronic narrowing of blood vessels, may lead to fatal heart failure and constitutes a major health threat. Acute myocardial infarction, triggered by coronary artery occlusion, produces cell necrosis over a time period of several hours. In the absence of reflow or sufficient perfusion, the cerebral or myocardial ischemic regions undergo progressive metabolic deterioration, culminating in infarction, whereas restoration of perfusion in the penumbra of the brain infarct or in the jeopardized but salvageable region of the myocardium may ameliorate the tissue damage.

Growth factor mediated improved perfusion of the penumbra in the brain or of the jeopardized myocardium of patients suffering ischemic events, either via increased vasodilation or angiogenesis (the formation of endothelial-lined vessels), may be of great therapeutic value according to Isner et al. in *J. Clin. Invest.* (1999) 103(9):1231–6 but many questions yet remain to be answered in this respect, for instance which suitable growth factor or combination of growth factors should be selected and which route of administration is effective yet safe for this purpose. In addition, an outstanding question is whether formation of new endothelial-lined vessels (i.e. angiogenesis) alone is sufficient to stimulate sustainable functional tissue perfusion. Indeed, coverage of endothelial-lined vessels by vascular smooth muscle cells (i.e. arteriogenesis) provides vasomotor control, structural strength and integrity and renders new vessels resistant to regression.

Capillary blood vessels consist of endothelial cells and pericytes, which carry all the genetic information required to form tubes, branches and entire capillary networks. Specific angiogenic molecules can initiate this process. A number of polypeptides which stimulate angiogenesis have been purified and characterized as to their molecular, biochemical and biological properties, as reviewed by Klagsbrun et al. in *Ann. Rev. Physiol.* (1991) 53:217–239 and by Folkman et al. in *J. Biol. Chem.* (1992) 267:10931–4. One factor that can stimulate angiogenesis and which is highly specific as a mitogen for vascular endothelial cells, is termed vascular endothelial growth factor (hereinafter referred as VEGF) according to Ferrara et al. in *J. Cell. Biochem.* (1991) 47:211–218. VEGF is also known as vasculotropin. Connolly et al. also describe in *J. Biol. Chem.* (1989) 264:20017–20024, in *J. Clin. Invest.* (1989) 84:1470–8 and in *J. Cell. Biochem.* (1991) 47:219–223 a human vascular permeability factor that stimulates vascular endothelial cells to divide in vitro and promotes the growth of new blood vessels when administered into healing rabbit bone grafts or rat corneas. The term vascular permeability factor (VPF for abbreviation) was adopted because of increased fluid leakage from blood vessels following intradermal injection and appears to designate the same substance as VEGF. The murine VEGF gene has been characterized and its expression pattern in embryogenesis has been analyzed. A persistent expression of VEGF was observed in epithelial cells adjacent to fenestrated endothelium, e.g. in chloroid plexus and kidney glomeruli, which is consistent with its role as a multifunctional regulator of endothelial cell growth and differentiation as disclosed by Breier et al. in *Development* (1992) 114:521–532. VEGF shares about 22% sequence identity, including a complete conservation of eight cysteine residues, according to Leung et al. in *Science* (1989) 246:1306–9, with human platelet-derived growth factor PDGF, a major growth factor for connective tissue. Alternatively spliced mRNAs have been identified for both VEGF and PDGF and these splicing products differ in their biological activity and receptor-binding specificity. VEGF is a potent vasoactive protein that has been detected in and purified from media conditioned by a number of cell lines including pituitary cells, such as bovine pituitary follicular cells (as disclosed by Ferrara et al. in *Biochem. Biophys. Res. Comm.* (1989) 161:851–858 and by Gospodarowicz et al. in *Proc. Natl. Acad. Sci. USA* (1989) 86: 7311–5), rat glioma cells (as disclosed by Conn. et al. in *Proc. Natl. Acad. Sci. USA* (1990) 87:1323–1327) and several tumor cell lines. Similarly, an endothelial growth factor isolated from mouse neuroblastoma cell line NB41 with an unreduced molecular mass of 43–51 kDa has been described by Levy et al. in *Growth Factors* (1989) 2:9–19.

VEGF was characterized as a glycosylated cationic 46 kDa dimer made up of two sub-units each with an apparent molecular mass of 23 kDa. It is inactivated by sulfhydryl reducing agents, resistant to acidic pH and to heating, and binds to immobilized heparin. VEGF has four different forms of 121, 165, 189 and 206 amino-acids due to alternative splicing of mRNA. The various VEGF species are encoded by the same gene. Analysis of genomic clones in the area of putative mRNA splicing also shows an intron/exon structure consistent with alternative splicing. The VEGF165 species is the molecular form predominantly found in normal cells and tissues. The VEGF 121 and VEGF165 species are soluble proteins and are capable of promoting angiogenesis, whereas the VEGF 189 and VEGF206 species are mostly cell-associated. All VEGF isoforms are biologically active, e.g. each of the species when applied intradermally is able to induce extravasation of Evans blue. However, VEGF isoforms have different biochemical properties which may possibly modulate the signalling properties of the growth factors. The VEGF 165, VEGF 189 and VEGF206 species contain eight additional cysteine residues within the carboxy-terminal region. The amino-terminal sequence of VEGF is preceded by 26 amino-acids corresponding to a typical signal sequence. The mature protein is generated directly following signal sequence cleavage without any intervening prosequence. Other VEGF polypeptides from the PDGF family of growth factors have been disclosed in U.S. Pat. No. 5,840,693. Purified and isolated VEGF-C cysteine deletion variants that bind to a VEGF tyrosine kinase receptor have been disclosed in U.S. Pat. No. 6,130,071.

Like other cytokines, VEGF can have diverse effects that depend on the specific biological context in which it is found. The expression of VEGF is high in vascularized tissues (e.g. lung, heart, placenta and solid tumors) and correlates with angiogenesis both temporally and spatially. VEGF has been shown to directly contribute to induction of angiogenesis in vivo by promoting endothelial cell growth during normal embryonic development wound healing, tissue regeneration and reorganization. Therefore VEGF has been proposed for use in promoting vascular tissue repair, as disclosed by EP-A-0,506,477. VEGF is also involved in pathological processes such as growth and metastasis of solid tumors and ischemia-induced retinal disorders such as disclosed in U.S. Pat. No. 6,114,320. VEGF expression is triggered by hypoxia so that endothelial cell proliferation and angiogenesis appear to be especially stimulated in ischemic areas. Finally, U.S. Pat. No. 6,040,157 discloses human VEGF2 polypeptides which have been putatively identified as novel vascular endothelial growth factors based on their amino-acid sequence homology to human VEGF. The latter document further discloses restoration of certain parameters in the ischemic limb by using a VEGF2 protein. However it is also known by Hariawala et al. in *J. Surg. Res.* (1996) 63(1):77–82 that a systemic administration of VEGF, in high doses over short periods of time, improves myocardial blood flow but produces hypotension in porcine hearts.

Placenta growth factor (hereinafter referred as PIGF) was disclosed by Maglione et al. in *Proc. Natl. Acad. Sci. USA* (1991) 88(20):9267–71 as a protein related to the vascular permeability factor. U.S. Pat. No. 5,919,899 discloses nucleotide sequences coding for a protein, named PIGF, which can be used in the treatment of inflammatory diseases and in the treatment of wounds or tissues after surgical operations, transplantations, burns of ulcers and so on. Soluble non-heparin binding and heparin binding forms, built up of 131 and 152 amino-acids respectively, have been described for PIGF which is expressed in placenta, trophoblastic tumors and cultured human endothelial cells, according to U.S. Pat. No. 5,776,755.

One problem to be solved by the present invention is to provide pharmaceutical compositions and methods for improving perfusion of the penumbra in the brain or perfusion of the jeopardized myocardium of patients suffering ischemic events, which will prove to be useful for the prevention and treatment of strokes and ischemic diseases, in particular ischemic cerebral infarction, acute myocardial infarction and chronic heart disease. Another problem to be solved by the present invention is to provide pharmaceutical compositions and methods for reducing or suppressing infarct expansion of the penumbra during ischemic cerebral infarction, making them useful for preventing and treating such a disease. Another problem to be solved by the present invention is to provide pharmaceutical compositions and methods for enhancing revascularization of acute myocardial infarcts, making them useful for preventing and treating such event. Another problem to be solved by the present invention is to provide a safe and effective route of administration of pharmaceutical compositions capable, namely with respect to the penumbra in the brain or the myocardium, of improving perfusion or reducing or suppressing infarct expansion or otherwise enhance revascularization of infarcts. Yet another problem to be solved by the present invention is to provide an effective means for the prevention and treatment of strokes and ischemic diseases, in particular ischemic cerebral infarction, acute myocardial infarction and chronic heart disease, which is devoid of adverse side-effects such as hypotension.

SUMMARY OF THE INVENTION

The various above-mentioned goals of the present invention have been successfully and unexpectedly satisfied by a suitable use of placenta growth factor and/or vascular endothelial growth factor or a fragment, derivative or homologue thereof such as disclosed hereinafter.

In a first aspect, the present invention relates to the use of placenta growth factor, a fragment, a derivative or a homologue thereof for the treatment of diseases such as strokes (including hemorrhagic strokes) and ischemic diseases in mammals. In a second aspect, the present invention relates to the use of vascular endothelial growth factor, a fragment, a derivative or a homologue thereof for the treatment of diseases such as strokes (including hemorrhagic strokes) and ischemic diseases in mammals. In a third aspect, the present invention relates to the use of compositions comprising: (a) placenta growth factor, a fragment, a derivative or a homologue thereof, and (b) vascular endothelial growth factor, a fragment, a derivative or a homologue thereof, as active ingredients in respective proportions such as to provide a synergistic effect in the prevention or treatment of strokes and ischemic diseases in mammals. The present invention also includes use of a placenta growth factor-vascular endothelial growth factor heterodimer.

Another aspect of the present invention is the use of a composition comprising: (a) placenta growth factor, a fragment, a derivative or a homologue thereof, and (b) vascular endothelial growth factor, a fragment, a derivative or a homologue thereof, for the manufacture of a medicine. The present invention also includes use of a placenta growth factor-vascular endothelial growth factor heterodimer.

Any of the above uses or any of the uses mentioned with respect to the present invention may be restricted to a non-medical use, a non-therapeutic use, a non-diagnostic use, a non-human use, or exclusively an in-vitro use, or a use with cells remote from an animal.

In another aspect, the present invention relates to pharmaceutical compositions for the prevention or treatment of strokes and ischemic diseases in mammals, comprising placenta growth factor, a fragment, a derivative or a homologue thereof as an active ingredient in admixture with at least a pharmaceutically acceptable carrier. In another aspect, the present invention relates to pharmaceutical compositions for the prevention or treatment of strokes and ischemic diseases in mammals, comprising vascular endothelial growth factor, a fragment, a derivative or a homologue thereof as an active ingredient in admixture with at least a pharmaceutically acceptable carrier. In yet another aspect, the present invention relates to pharmaceutical compositions comprising:

(a) placenta growth factor, a fragment, a derivative or a homologue thereof, and (b) vascular endothelial growth factor, a fragment, a derivative or a homologue thereof, as active ingredients in respective proportions such as to provide a synergistic effect in the prevention or treatment of strokes and ischemic diseases in mammals, in admixture with a pharmaceutically acceptable carrier. The present invention also includes use of a placenta growth factor-vascular endothelial growth factor heterodimer.

The present invention further relates to a method of treatment or prevention of a stroke (including a hemorrhagic stroke) or an ischemic disease in a mammal, comprising administering to the mammal in need of such treatment or prevention a therapeutically effective amount of placenta growth factor, a fragment, a derivative or a homologue thereof. The present invention also relates to a method of treatment or prevention of a stroke (including a hemorrhagic stroke) or an ischemic disease in a mammal, comprising administering to the mammal in need of such treatment or prevention a therapeutically effective amount of vascular endothelial growth factor, a fragment, a derivative or a homologue thereof. Finally, the present invention relates to a method of treatment or prevention of a stroke (including a hemorrhagic stroke) or an ischemic disease in a mammal, comprising administering to the mammal in need of such treatment or prevention a therapeutically effective amount of (a) placenta growth factor, a fragment, a derivative or a homologue thereof, and (b) vascular endothelial growth factor, a fragment, a derivative or a homologue thereof, in respective proportions such as to provide a synergistic effect in such prevention or treatment. The present invention also includes use of a placenta growth factor-vascular endothelial growth factor heterodimer.

DEFINITIONS

In all of the various aspects of the present invention, the terms "stroke" and "ischemic disease" have the meanings and definitions as given in the section BACKGROUND OF THE INVENTION. Examples of ischemic diseases within the scope of this invention include, among others:

ischemic stroke or focal ischemic cerebral infarction, acute myocardial infarction or coronary ischemia, chronic ischemic heart disease, ischemic disease of an organ other than myocardium or a region of the brain, for instance a peripheral limb (e.g. limb ischemia or peripheral arterial disease).

In all of the various aspects of the present invention, the term "mammal" is considered in its common meaning and includes namely humans, equines, felines, canines, porcines, bovines, ovines and the like.

The term "homologue" as used herein with reference to growth factors of the present invention refers to molecules having at least 50%, more preferably at least 70% and most preferably at least 90% amino acid sequence identity with the relevant growth factor. With respect to vascular endothelial growth factor, it includes both the dimer and the sub-unit thereof.

The term "fragment" as used herein with reference to growth factors of the present invention refers to molecules which contain the active portion of the growth factor, i.e. the portion which is functionally capable of improving perfusion or reducing or suppressing infarct expansion or otherwise enhancing revascularization of infarcts, and which may have lost a number of non-essential (with respect to angiogenesis and/or arteriogenesis) properties of the parent growth factor. Preferably the fragment used in the present invention is the angiogenetic and/or arteriogenetic fragment of the relevant growth factor.

The term "derivative" as used herein with reference to growth factors of the present invention refers to molecules which contain at least the active portion of the growth factor (as defined hereinabove) and a complementary portion which differs from that present in the wild-type growth factor, for instance by further manipulations such as introducing mutations.

The term "vascular endothelial growth factor" as used herein refers, whether of human or animal origin, to all isoforms thereof such as disclosed in the section BACKGROUND OF THE INVENTION. However the 165 amino-acids isoform is preferred. The term "placenta growth factor" as used herein refers, whether of human or animal origin, to all isoforms thereof, namely the 131 and 152 amino-acids forms disclosed above.

DETAILED DESCRIPTION OF THE INVENTION

In the methods of treatment or prevention constituting various aspects of the present invention, the administration of active ingredient(s) may be chronic or intermittent, depending on the medical status and need of the mammal. The active ingredient(s) may be provided to the patient by oral, intranasal, subcutaneous, intramuscular, intradermal, intravenous, intraarterial or parenteral administration or by catheterization, preferably subcutaneously. However the most preferred mode of administration is a chronic continuous subcutaneous delivery such as by means of an osmotic pump. The term "therapeutically effective amount" as used herein preferably means an amount capable of improving perfusion or reducing or suppressing infarct expansion or otherwise enhancing revascularization of infarcts, and more preferably an amount of about 2 to 2,000 µg per kg of body weight of the mammal to be treated and per week for each active ingredient. In the various aspects of the present invention where both placenta growth factor and vascular endothelial growth factor are present as biologically active ingredients (a) and (b) respectively, they are preferably used as a combined preparation comprising from about 1 to about 99% by weight of ingredient (a) and from about 1 to about 99% by weight of ingredient (b) for simultaneous, separate or sequential use.

In view of the fact that ingredients (a) and (b) do not necessarily bring out their joint therapeutic effect directly at the same time in the mammal to be treated or prevented, the pharmaceutical compositions of the present invention which comprise both ingredients (a) and (b) may be in the form of a medical kit or package containing the two ingredients in separate but adjacent form. In the latter context, each of ingredients (a) and (b) may therefore be formulated in a way suitable for an administration route different from that of the other ingredient.

In the pharmaceutical compositions constituting various aspects of the present invention, the term "pharmaceutically acceptable carrier" means any material or substance with which the active ingredient(s) is formulated in order to facilitate its application or dissemination, for instance by dissolving, dispersing or diffusing the said ingredient, and/or to facilitate its storage, transport or handling without impairing its effectiveness. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, pellets or powders. However a formulation suitable for subcutaneous use is highly preferred.

Suitable pharmaceutical carriers for use in the present compositions are well known to those skilled in the art, and there is no particular restriction to their selection within the invention. They may also include additives such as wetting agents, dispersing agents, stickers, adhesives, emulsifying agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals. The pharmaceutical compositions of the present invention may be prepared in any known manner, for instance by homogeneously mixing, coating and/or grinding the active ingredients, in a one-step or multi-steps procedure, with the selected carrier material and, where appropriate, the other additives such as surface-active agents. may also be prepared by micronisation, for instance in view to obtain them in the form of microspheres usually having a diameter of about 1 to 10 μm, namely for the manufacture of microcapsules for controlled or sustained release of the active ingredients.

Suitable surface-active agents to be used in the pharmaceutical compositions of the present invention are non-ionic, cationic and/or anionic materials having good emulsifying, dispersing and/or wetting properties. Suitable anionic surfactants include both water-soluble soaps and water-soluble synthetic surface-active agents. Suitable soaps are alkaline or alkaline-earth metal salts, unsubstituted or substituted ammonium salts of higher fatty acids ($C_{10}$–$C_{22}$), e.g. the sodium or potassium salts of oleic or stearic acid, or of natural fatty acid mixtures obtainable form coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, unsubstituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives preferably contain 8 to 22 carbon atoms. Examples of alkylarylsulphonates are the sodium, calcium or alcanolamine salts of dodecylbenzene sulphonic acid or dibutyl-naphtalenesulphonic acid or a naphtalene-sulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidylglycerine, lysolecithin, cardiolipin, dioctanylphosphatidyl-choline, dipalmitoylphoshatidyl-choline and their mixtures.

Suitable non-ionic surfactants include polyethoxylated and polypropoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with poylypropylene glycol, ethylenediaminopolypropylene glycol containing 1 to 10 carbon atoms in the alkyl chain, which adducts contain 20 to 250 ethyleneglycol ether groups and/or 10 to 100 propyleneglycol ether groups. Such compounds usually contain from 1 to 5 ethyleneglycol units per propyleneglycol unit. Representative examples of non-ionic surfactants are nonylphenol—polyethoxyethanol, castor oil polyglycolic ethers, polypropylene/polyethylene oxide adducts, tributylphenoxypolyethoxyethanol, polyethyleneglycol and octylphenoxypolyethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants include quaternary ammonium salts, preferably halides, having 4 hydrocarbon radicals optionally substituted with halo, phenyl, substituted phenyl or hydroxy; for instance quaternary ammonium salts containing as N-substituent at least one $C_8$–$C_{22}$ alkyl radical (e.g. cetyl, lauryl, palmityl, myristyl, oleyl and the like) and, as further substituents, unsubstituted or halogenated lower alkyl, benzyl and/or hydroxy-lower alkyl radicals.

A more detailed description of surface-active agents suitable for this purpose may be found for instance in "McCutcheon's Detergents and Emulsifiers Annual" (MC Publishing Crop., Ridgewood, N.J., 1981), "Tensid-Taschenbuch", $2^{nd}$ ed. (Hanser Verlag, Vienna, 1981) and "Encyclopaedia of Surfactants (Chemical Publishing Co., New York, 1981).

Additional ingredients may be included in order to control the duration of action of the active ingredient in the pharmaceutical composition of the invention. Control release compositions may thus be achieved by selecting appropriate polymer carriers such as for example polyesters, polyamino acids, polyvinyl pyrrolidone, ethylene-vinyl acetate copolymers, methylcellulose, carboxymethylcellulose, protamine sulfate and the like. The rate of drug release and duration of action may also be controlled by incorporating the active ingredient into particles, e.g. microcapsules, of a polymeric substance such as hydrogels, polylactic acid, hydroxymethylcellulose, polymethyl methacrylate and the other above-described polymers. Such methods include colloid drug delivery systems like liposomes, microspheres, microemulsions, nanoparticles, nanocapsules and so on. Depending on the route of administration, the pharmaceutical composition may also require protective coatings.

Pharmaceutical forms suitable for injectionable use include sterile aqueous solutions or dispersions and sterile powders for the extemporaneous preparation thereof. Typical carriers for this purpose therefore include biocompatible aqueous buffers, ethanol, glycerol, propylene glycol, polyethylene glycol and the like and mixtures thereof.

Without wishing to be bound by theory it is believed, based on the following experimental evidence, that although the absence of both PIGF alleles does not cause detectable vascular defects, however placenta growth factor (PIGF) is required to mediate the effect of vascular endothelial growth factor (VEGF) in endothelial and smooth muscle cell growth, migration and survival. Furthermore, the absence of PIGF appears to significantly impair VEGF-mediated angiogenesis and arteriogenesis during various pathological processes in vivo. Thus PlGF is an attractive alternative therapeutic agent for VEGF, that only stimulates vascular growth at angiogenic sites of increased VEGF expression, without causing systemic effects such as hypotension or generalized edema.

The following experimental data will prove that the cerebral infarct size caused by occlusion of the middle cerebral artery (hereinafter referred as MCA) in mice is markedly reduced by continuous subcutaneous delivery of PlGF (which can be obtained from various sources such as R&D, Abingdon, United Kingdom; Pharma Biotechnologie, Hannover, Germany; ICN, Costa Mesa, Calif.; and Geymonat SpA, Anagni, Italy), VEGF (for instance rVEGF$_{165}$ can be obtained—amongst others—from R&D, Abingdon, UK; Santa Cruz Biotechnology Inc., Santa Cruz, Calif.; Pharma Biotechnologie, Hannover, Germany; ICN, Costa Mesa, Calif.; Endogen, Woburn, Mass.; Harlan Sera Laboratories, LeicesterShire, United Kingdom; Peprotech, Rocky Hill, N.J.), or preferably both in combination, via an osmotic minipump. In addition, revascularization of ischemic myocardium after occlusion of the left coronary artery (hereinafter referred as LCA) is also significantly improved by continuous subcutaneous delivery of PlGF, VEGF (rVEGF$_{165}$) or both, via an osmotic minipump. Chronic delivery of small amounts of PlGF was found to be at least as effective as VEGF to reduce ischemic infarct size. Furthermore, co-administration of both VEGF and PlGF was more effective than anticipated from either growth factor alone. These data show that VEGF, preferably PlGF or both in combination, can be successfully used for the treatment and prevention of strokes and ischemic diseases, in particular ischemic stroke and acute myocardial infarction, without putting the patient at risk of adverse side effects.

Various embodiments of the present invention will be demonstrated in more details in the following examples, which are however not intended to be limiting to the scope of the invention.

EXAMPLE 1

Protection Against Cerebral Ischemic Infarct Expansion by Chronic Administration of VEGF, PlGF or a Combination of Both Animal experiments were conducted according to the guiding principles of the American Physiological Society and the International Committee on Thrombosis and Haemostasis as published by A. Giles in *Thromb. Haemost.* (1987) 58:1078–1084. Focal cerebral ischemia was produced by persistent occlusion of the MCA according to Welsh et al. in *J. Neurochem.* (1987) 49:846–51. Briefly, mice of either sex weighing 20 to 30 g, with a genetic background of 50% Swiss/50% 129 were anesthetized by intraperitoneal injection of ketamine (75 mg/ml, available from Apharmo, Arnhem, Netherlands) and xylazine (5 mg/ml, available from Bayer, Leverkusen, Germany). Atropine (1 mg/kg, available from Federa, Brussels, Belgium) was administered intramuscularly and body temperature was maintained by keeping the animals on a heating pad. A "U" shape incision was made between the left ear and left eye. The top and backside segments of the temporal muscle were transsected and the skull was exposed by retraction of the temporal muscle. A small opening (1 to 2 mm diameter) was made in the region over the MCA with a hand-held drill, with saline superfusion to prevent heat injury. The meningae were removed with a forceps and the MCA was occluded by ligation with 10-0 nylon thread (available from Ethylon, Neuilly, France) and transsected distally to the ligation point. Finally, the temporal muscle and skin were sutured back in place. The animals were allowed to recover and were then returned to their cages. Infarcted mice were treated with saline (for control), PlGF (715 ng/day), VEGF days (425 ng/day) or the combination of both, using an osmotic minipump (Alzet type 2001, Broekman Institute, Someren, Netherlands), subcutaneously implanted on the back, so that the growth factors were continuously delivered over a period of 7 days. After that period, the animals were sacrificed with an overdose of Nembutal (500 mg/kg, available from Abbott Laboratories, North Chicago, Ill.), perfusion fixed via the left ventricle with 4% formalin in phosphate buffer saline, and decapitated. The brain was removed, processed for histology as described by P. Carmeliet et al. in *Nature* (1996) 380:435–439, *Nature* (1996) 383:73–75 and *Nature* (1998) 394:485–490 and immune-stained for microtubule-associated protein-2 (hereinafter referred as MAP2), a structural protein that disappears early during irreversible ischemic death. MAP-2 negative infarct areas throughout the brain were morphometrically quantified at 420 μm distances using a dedicated image analysis system (Quantimed 6000, available from Leica). The infarct volume was defined as the sum of the unstained areas of the sections multiplied with their thickness. The data of these experiments, presented in table 1 below, are the mean±standard error of mean (SEM) values of the infarct size expressed in mm$^3$ and used as a means for measuring cerebral infarction, including the number of observations between brackets and wherein an asterisk means p=0.001 vs. control. The significance of differences was determined by unpaired t-test.

TABLE 1

| Treatment group | Infarct size |
| --- | --- |
| Control | 12 ± 1.7 (7) |
| PlGF + VEGF | 4.6 ± 1.3 (8)* |
| PlGF | 8.0 ± 2.9 (4) |
| VEGF | 7.6 ± 2.5 (3) |

Intracerebral bleeding was not observed in any of the mice. Taken together, these data indicate that VEGF and PlGF and, even more, their combination are effective in suppressing infarct expansion of the penumbra.

EXAMPLE 2

Murine Acute Myocardial Infarction Model

Myocardial infarction was inflicted by permanent ligation of the left coronary artery (LCA) as described by Lutgens et al. in *Cardiovasc. Res.* (1999) 41:586–59. Briefly, mice were anesthetized by intraperitoneal injection of 60 mg/kg sodium pentobarbital. The animals were placed in a supine position, intubated with a blunted 21 Gauge needle, and placed on positive-pressure respiration with a tidal volume of 1.0 ml at a respiratory rate of 100/min, using a Rodent Ventilator, model 683 (available from Harvard Apparatus Inc., Holliston, Mass.). A transverse skin incision above the third intercostal space and a left thoracotomy between the third and fourth ribs were made, and a 6.0 filament was tied around the LCA about 1 mm distal from the tip of the left auricle. Slight rotation of the animal to the right, oriented the heart to better expose the left ventricle. After closure of the chest cavity and re-expansion of the lungs using positive pressure at end expiration, the infarcted mice were allowed to recover on a warming pad.

An osmotic minipump (Alzet type 2001, available from Broekman Institute, Someren, Netherlands), delivering VEGF, PlGF or both, during 7 days was implanted subcutaneously on the back of the mouse immediately after performance of myocardial infarction. Surgical wounds healed with no apparent infection. Perioperative mortality was 10%.

At 7 days after surgery, infarcted mice were anesthetized as described above, perfused with 0.9% saline, and perfusion-fixed with 1% paraformaldehyde in 0.1 M phosphate buffered saline (pH 7.0) via the abdominal aorta at physiological pressure. Before perfusion fixation, hearts were injected with 100 μl 0.1 M cadmium chloride to arrest the heart in a relaxed state. Fixed hearts were dissected and prepared for histology as described by Heymans et al. in *Nat. Med.* (1999) 5(10):1135–1142.

6 μm-thin sections were used for haematoxylin-eosin staining. Endothelial cells were stained for thrombomodulin (thrombomodulin antibodies from Harvard University, Boston, Mass.), whereas vascular smooth muscle cells were stained for smooth muscle alpha-actin (Sigma), as described by Heymans et al. (cited supra). The numbers of vessels per infarct were counted morphometrically using a Quantimet Q600 image analysis system (available from Leica, Brussels, Belgium).

EXAMPLE 3

Enhanced Revascularization of Acute Myocardial Infarcts by Chronic Administration of VEGF, PlGF, or a Combination of Both in Mice The therapeutic effect of VEGF and PlGF was tested by delivering these growth factors continuously over 7 days by the method described in example 2. Results of these tests are presented in tables 2 and 3 below, wherein:

table 2 provides the number of vessels (mean+SEM values), identified by thrombomodulin staining of endothelial cells as a measure of angiogenesis, throughout the infarct in groups of 8 to 10 mice each. An asterisk means p<0.05 vs. control.

table 3 provides the number of vessels (mean+SEM values), identified by smooth muscle alpha-actin staining of endothelial cells as a measure of arteriogenesis, throughout the infarct in groups of 8 to 10 mice each. An asterisk means p<0.05 vs. control.

TABLE 2

| | Vessels per infarct | | |
|---|---|---|---|
| Growth factor | Small vessels | Medium vessels | Large vessels |
| Control | 225 ± 20 | 50 ± 4 | 33 ± 3 |
| PlGF (715 ng/day) | 500 ± 45* | 81 ± 7* | 47 ± 4* |
| PlGF (3.5 μg/day) | 410 ± 50* | 115 ± 19* | 61 ± 6* |
| VEGF (450 ng/day) | 370 ± 40* | 85 ± 7* | 42 ± 2* |
| PlGF (715 ng/day) + VEGF (450 ng/dy) | 470 ± 100* | 110 ± 8* | 67 ± 3* |

They show that the treatment of infarcted mice with 715 ng/day PlGF dimer stimulated the formation of new endothelial-lined vessels (angiogenesis) and the maturation of these coronary vessels by coverage with vascular smooth muscle cells (arteriogenesis) in the ischemic myocardium better, in all types of vessels, than the treatment of infarcted mice with 430 ng/day VEGF dimer. A higher dose (3.5 μg/day) of PlGF dimer also improved infarct angiogenesis and arteriogenesis.

TABLE 3

| | Vessels per infarct | | |
|---|---|---|---|
| Growth factor | Small vessels | Medium vessels | Large vessels |
| Control | 88 ± 4 | 17 ± 2 | 11 ± 2 |
| PlGF (715 ng/day) | 140 ± 36* | 30 ± 7* | 14 ± 3 |
| PlGF (3.5 μg/day) | 120 ± 18* | 44 ± 10* | 19 ± 3* |
| VEGF (450 ng/day) | 104 ± 19 | 26 ± 5* | 11 ± 2 |
| PlGF (715 ng/day) + VEGF (450 ng/dy) | 111 ± 7* | 38 ± 4* | 22 ± 2* |

EXAMPLE 4

Enhanced Revascularization of Acute Myocardial Infarcts by Chronic Administration of VEGF, PlGF, or a Combination of Both in Urokinase-type Plasminogen Activator Deficient Mice Synergism between PlGF and VEGF in stimulating angiogenesis and arteriogenesis in ischemic myocarium was tested in infarcted mice lacking urokinase-type plasminogen activator (u-PA$^{+/-}$), since these mice are resistant to therapeutic angiogenesis by VEGF alone. Treatment of u-PA$^{+/-}$ mice with a combination of VEGF (450 ng/day) and PlGF (3.5 μg/day) was more effective than VEGF (450 ng/day) or PlGF (3.5 μg/day) alone in improving myocardial angiogenesis and arteriogenesis, as shown in tables 4 and 5 providing results in the same manner as tables 2 and 3 respectively.

TABLE 4

| | Vessels per infarct | | |
|---|---|---|---|
| Growth factor | Small vessels | Medium vessels | Large vessels |
| Control | 220 ± 15 | 48 ± 4 | 34 ± 3 |
| PlGF (3.5 μg/24 h) | 260 ± 17 | 55 ± 8 | 37 ± 4 |
| VEGF (450 ng/24 h) | 170 ± 20 | 64 ± 9 | 44 ± 4 |
| PlGF (715 ng/24) + VEGF (450 ng/24 h) | 320 ± 39* | 100 ± 13* | 65 ± 8* |

TABLE 5

| | Vessels per infarct | | |
|---|---|---|---|
| Growth factor | Small vessels | Medium vessels | Large vessels |
| Control | 88 ± 5 | 21 ± 2 | 11 ± 2 |
| PlGF (3.5 μg/day) | 72 ± 11 | 22 ± 2 | 20 ± 3* |
| VEGF (450 ng/day) | 82 ± 6 | 20 ± 2 | 8 ± 1 |
| PlGF (715 ng/day) + VEGF (450 ng/dy) | 115 ± 8* | 32 ± 4* | 23 ± 6* |

EXAMPLE 5

Side Effects of PlGF Versus VEGF Administration

Mean arterial blood pressure (MAP), measured using high-fidelity pressure micromanometers (Millar Instruments, Houston, Tex.) was 93±5 mm Hg in control mice. Bolus intravenous injection of 3 μg active VEGF dimer caused significant hypotension (68±3 mm Hg; p<0.05). Bolus administration of 5 μg active PlGF dimer did not reduce arterial bood pressure (91±11 mm Hg). These data indicate that upon acute administration of 3 μg amounts, PlGF has no systemic hemodynamic side effects, whereas VEGF decreases blood pressure.

EXAMPLE 6

Use of PlGF-VEGF Heterodimers

VEGF and PlGF have to bind as dimers to their cognate receptors. The activity of VEGF/VEGF-homodimers and PlGF/PlGF-homodimers is described above. However, VEGF and PlGF can also form heterodimers and have been documented in vivo (Cao, Y., Linden, P., Shima, D., Browne, F. & Folkman, J. In vivo angiogenic activity and hypoxia induction of heterodimers of placenta growth factor/vascular endothelial growth factor. J Clin Invest 98, 2507–11, 1996; DiSalvo, J. et al. Purification and characterization of a naturally occurring vascular endothelial growth factor placenta growth factor heterodimer. J Biol Chem 270, 7717–23, 1995). Their role in angiogenesis and arteriogenesis in vivo remains controversial, and no information is available whether VEGF/PlGF heterodimers can be used for therapeutic applications.

Using the same model of infarct revascularization as exemplified in Table 2 and Table 3 of example 3, VEGF/PlGF heterodimer (from R&D, Abbingdon, UK) was administered via osmotic minipumps for a week at a dose of 10 microgram VEGF/PlGF heterodimer in wild type mice. The experimental data is reported in tables 6 and 7 as vessels/mm2 instead of as vessels/infarct. However the tables may be interpreted qualitatively in the same way as previous tables.

TABLE 6

Endothelial-lined vessels (angiogenesis)

| | Vessels per mm$^2$ | | |
|---|---|---|---|
| Growth factor | Small vessels | Medium vessels | Large vessels |
| Control | 78 ± 2 | 25 ± 4 | 21 ± 3 |
| VEGF-PlGF heterodimer | 170 ± 25 | 51 ± 7 | 37 ± 4 |

TABLE 7

Smooth-muscle-lined vessels (arteriogenesis)

| | Vessels per mm$^2$ | | |
|---|---|---|---|
| Growth factor | Small vessels | Medium vessels | Large vessels |
| Control | 25 ± 3 | 9 ± 1 | 5 ± 1 |
| VEGF-PlGF heterodimer | 38 ± 3 | 19 ± 2 | 9 ± 1 |

All values are statistically significant (p<0.05; treatment versus control)

What is claimed is:

1. A method for reducing infarct size during treatment of an ischemic disease in a mammal comprising administering to said mammal one of placenta growth factor, a fragment, a derivative or a homologue thereof having at least 70% amino-acid sequence identity with placenta growth factor as the active ingredient in admixture with a pharmaceutically acceptable carrier.

2. The method according to claim 1, wherein said schemic disease is stroke.

3. The method according to claim 1, wherein said ischemic disease is acute myocardial infarction.

4. The method according to claim 1, wherein the use includes use after a cerebral event with which the medical indication includes both ischemic and hemoraghic stroke.

5. The method according to claim 1, wherein said pharmaceutical composition is administered chronically.

6. The method according to claim 1, wherein said pharmaceutical composition is administered intermittently.

7. The method according to claim 1, wherein each growth factor is administered by oral, intranasal, subcutaneous, intramuscular, intradermal, intravenous, intraarterial or parenteral administration or by catheterization.

8. The method according to claim 1, wherein a therapeutically effective amount of the pharmaceutical composition is an amount of 2 to 2,000 μg per kg of body weight of the said mammal and per week.

9. A method for the reduction of infarct size in the treatment of an ischemic disease in a mammal, comprising administering to the mammal in need of such treatment or prevention a therapeutically effective amount of placenta growth factor, a fragment, a derivative or a homologue thereof having at least 70% amino-acid sequence identity with placenta growth factor.

10. The method according to claim 9, wherein said administration is one of a chronic and an intermittent administration.

11. The method according to claim 9, wherein said placenta growth factor is administered by one of oral, intranasal, subcutaneous, intramuscular, intradermal, intravenous, intra-arterial or parenteral administration and by catheterization.

12. The method to claim 9, wherein a therapeutically effective amount of 2 to 2,000 μg per kg of body weight of the said mammal and per week.

13. The method according to claim 1, wherein said pharmaceutical composition is systemically hemodynamically stable.

* * * * *